United States Patent [19]

Affeldt et al.

[11] Patent Number: 4,873,988

[45] Date of Patent: Oct. 17, 1989

[54] VASOMETRIC TEST APPARATUS FOR TESTING BLOOD SUPPLY TO THE TOE OF A PATIENT

[75] Inventors: Karl-Heinz Affeldt; Ulrich Hantel, both of Berlin, Fed. Rep. of Germany

[73] Assignee: Robert Bosch GmbH, Stuttgart, Fed. Rep. of Germany

[21] Appl. No.: 194,463

[22] Filed: May 16, 1988

[30] Foreign Application Priority Data

May 21, 1987 [DE] Fed. Rep. of Germany ....... 3717046

[51] Int. Cl.$^4$ .............................................. A61B 5/02
[52] U.S. Cl. ................................... 128/687; 128/691; 128/666
[58] Field of Search ................. 128/26, 663, 637, 664, 128/665, 666, 667, 672, 687, 691, 694, 774, 779, 782; 248/346

[56] References Cited

U.S. PATENT DOCUMENTS

| | | | |
|---|---|---|---|
| 1,371,747 | 3/1921 | Fischer | 248/346 |
| 4,183,360 | 1/1980 | Carlson | 128/666 |
| 4,425,922 | 1/1984 | Conti | 128/691 |
| 4,454,885 | 6/1984 | Reddy | 128/691 |
| 4,509,528 | 4/1985 | Sahota | 128/691 |

Primary Examiner—Max Hindenburg
Assistant Examiner—John D. Zele
Attorney, Agent, or Firm—Frishauf, Holtz, Goodman & Woodward

[57] ABSTRACT

To provide for adjusted positioning of a pulse sensor (50) against the selected toe of a patient, while the patient is relaxed, and without applying substantial pressure of the sensor against the toe, a base plate is formed with a depression to receive the heel of the foot of the user, and a support element (20) is adjustably positioned on a pair of parallel vertically extending posts (17, 18), projecting from the base plate. The support element is a transverse structure, slidable on the posts, and having a shaft (30) to which a bail (42) is attached. The pulse sensor (50) is mounted on the horizontal portion (48) of the bail, and is slidable along and rotatable about the portion (48). In addition, the bail (42) is slidable sideways (B) with respect to the foot of the user, i.e. across the toes, movable back and forth with respect to the toe to be tested while the pulse sensor (50) is retained against the toe by a spring (34) biasing the shaft, and hence the bail, towards the toe. This permits movement of the pulse sensor in three dimensions as well as tilting and rotating the pulse sensor with respect to the toe (61).

17 Claims, 2 Drawing Sheets the arrangement has the advantage that the patient can rest the foot and maintain it completely relaxed and motionless. The toe is in contact with the sensing element and remains motionless. The sensor, due to its resilient support, applies only very small resilient biasing force against the toe. The biasing force, preferably, is adjustable so that the engagement force of the volume pulse sensor can be matched to the physical condition of the patient.

VASOMETRIC TEST APPARATUS FOR TESTING BLOOD SUPPLY TO THE TOE OF A PATIENT

Reference to related application by the inventor hereof and assigned to the assignee of the present invention, the disclosure of which is hereby incorporated by reference: U.S. Ser. No. 07/194,462, filed May 16, 1988, AFFELDT et al

Reference to related publication

Prof. Völker, "Herz- and Gefässerkrankungen", Kreislaufbücherei English translation by H. Mayer, M.D., Stanford University, "Cardiac and Vascular Disorders", published by Charles C. Thomas, Copyright 1965.

The present invention relates to vasometric test apparatus, and more particularly to such apparatus to test interferences with blood flow by means of vasography.

BACKGROUND

Testing for interference with blood circulation is known, see the publication Prof. Völker, "Cardiac and Vascular Disorders" (English translation by Henry Mayer, M.D., published by Charles C. Thomas, second edition, Copyright 1965). The apparatus used is usually termed vasometric apparatus, to determine such interferences by vasography. A light sensor, which may be responsive to transmitted or reflected light is applied for example, to a toe of the person to be tested. The sensor is responsive to check the volume pulse of blood flow and provide representative electrical signals. The electrical signals, after amplification, are then displayed on a display monitor as a curve, or recorded on a curve drawing recording instrument. Curves are obtained from the right as well as the left side of the person to be tested, and upon comparison of the curves of similar digits, it is possible to determine the condition of blood vessels.

The measuring method described is subject to errors, in that the measuring result depends on the sensor as applied to the toe of the person to be tested, as well as on the maintenance of the foot in quiet and relaxed condition while the measuring takes place.

The digits to be tested may be the fingers or the toes of the person to be tested.

THE INVENTION

It is an object to provide an apparatus which retains the toes of a foot in loose, relaxed and yet fixed position, while retaining a sensor against the toe with only small mechanical bias or pressure, so that the expansion of blood vessels, and particularly small artery vessels is not affected by the testing apparatus.

Briefly, a base plate is formed with a depression to receive the heel of the foot of the patient, with the patient in a reclining position, for example on a stretcher or an examining table. An upstanding support structure extends from the base plate, essentially parallel to the foot of the patient who is lying on the examining table, that is, essentially at a right angle to the base plate. A support element is adjustably positioned on the support structure, the support element retaining a pulse sensor having a sensing surface thereon. The sensor is movable on the support element, for movement in three dimensions, that is, up-down, right-left, and towards-and-away from the foot of the user. The support element is resiliently held, so that the pressure of the pulse sensor against the back of the toe of the user can be so adjusted that practically no disturbances in blood flow occur due to the test itself.

Drawings, showing an illustrative embodiment

DETAILED DESCRIPTION

Figure 1:
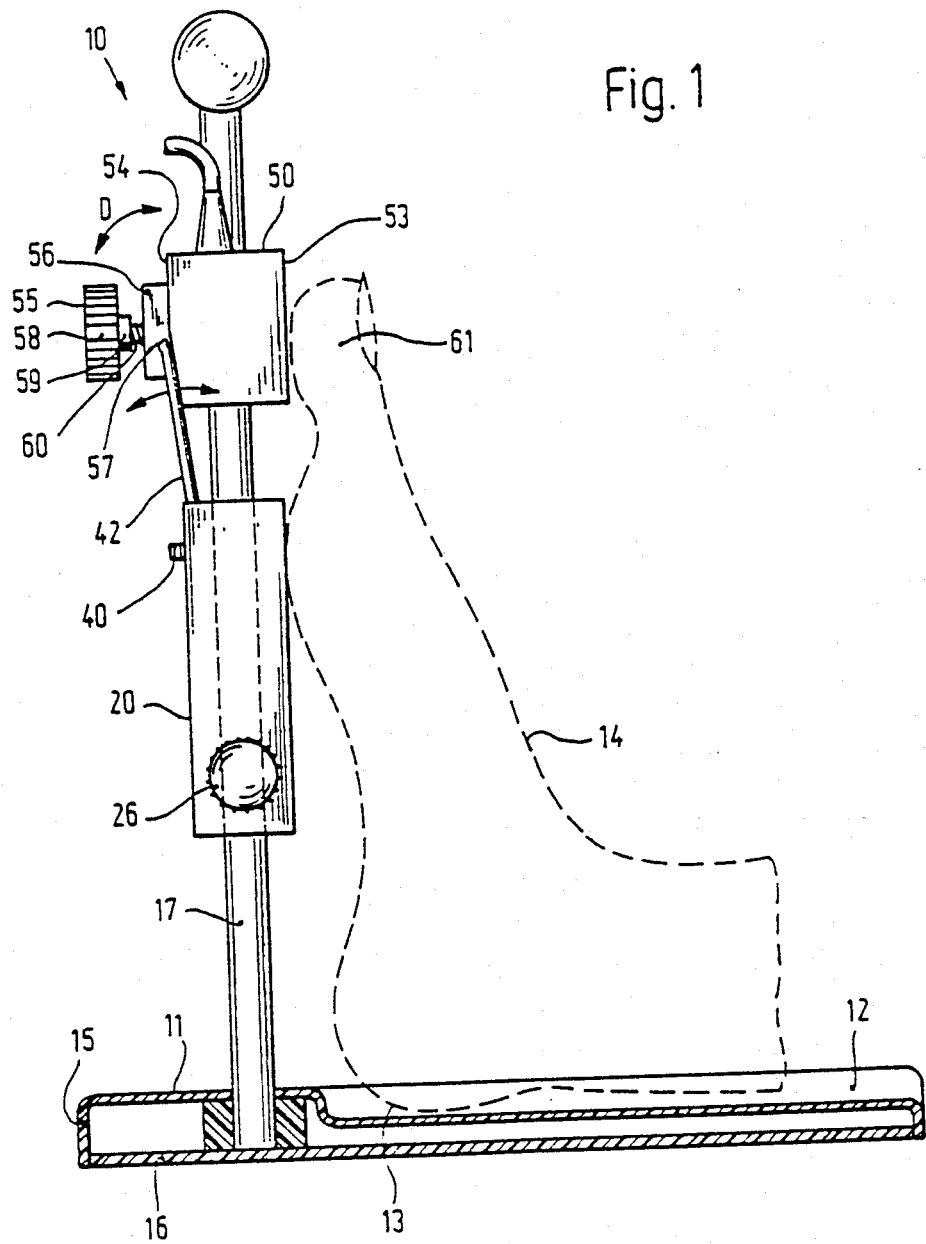
FIG. 1 is a part-sectional vertical longitudinal view of the apparatus, in which the foot of a patient is shown in broken lines to permit ready association of the apparatus to the anatomy of the patient.

The vasometric apparatus 10 has a horizontal base plate 11 which is formed with an elongated bowl-shaped depression 12 to receive the heel 13 of the foot 14 of a patient. The base plate is formed as a flat, shallow, hollow structure 15 having a flat base 16, a closing structure 15. Two vertical posts 17, 18 are secured to the base. A support element 20 extends transversely between the two posts 17, 18, and is slidably retained thereon, for vertical shifting, which may be referred to as movable in a z-axis. The support element 20 includes a trough or tub-shaped longitudinal housing 21 which has a back wall 22 for supporting the patient's foot. Two vertical slides or sleeves 23, 24 are secured to the back wall 22, and formed with suitable longitudinal slide bores 25, to receive the respective posts 17, 18.

The support element 20 can be locked in vertical or z axis adjusted position by a clamping screw 26, passing through an opening 27 in the housing 21 and screwed into a tapped hole 28 in the bearing sleeve 24. Two such screws may be provided, one in each of the bearing sleeves 23, 24. The screw 26 can lock the support element 20 in any suitable height-adjusted position above the base plate 11 and/or the depression 12 which receives the heel of the patient.

A horizontal shaft 30 extends transversely between the bearing sleeves or sliders 23, 24. The shaft 30 has ends 31 of lesser diameter than the rest of the shaft, and fitted into suitable bores 32 of the bearing sleeves or sliders 23, 24. Shaft 30 is rotatable about a pivot axis transverse to the extent of the posts 17, 18. A radial pin 33 is located in the center of the shaft 30; it need not be placed exactly in the center, and other positions are possible. Pin 33 is coupled to an end of a tension spring 34. The other end of the tension spring 34 is coupled to one end of a threaded bolt 35 (see FIG. 3) which is fitted in an opening 36 of a horizontal leg 37 of an angle element 38. A nut 40 is screwed in the upper end of the bolt 35, the nut having a knurled circumference to be accessible by an operator for the apparatus. The vertical leg 39 of the angle element 38 is secured to the back wall 22 of the housing 21.

An essentially U-shaped frame element 42 is secured to the shaft 30. Frame 42 extends radially from the shaft 30, roughly perpendicularly to the radial pin 33. The U-shaped element 42 preferably is a wire element, having longitudinal legs 43, 44 which extend through elongated openings 45, 46 of the upper or top surface 47 of the tub or trough-like housing 21. The element 42 is completed by a horizontal portion 48. A volume sensor 50, preferably a reflection light sensor, is secured to the horizontal or cross element 48 of the frame 42, which forms a support bail.

Figure 3:
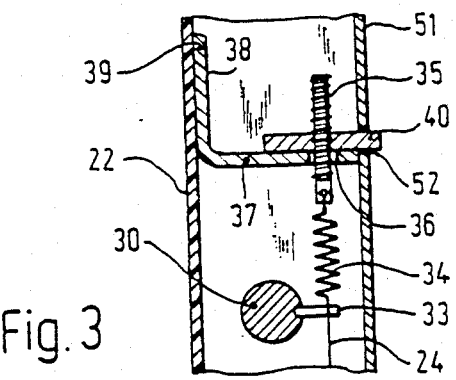
FIG. 3 is a section along line III—III of FIG. 2, to a different scale, and showing some elements exaggerated for ease of illustration.

A plate 51 can be provided to close off the trough-shaped housing 21, formed with an elongated slot 52 to permit external access to the adjustment wheel or nut 40 (see FIG. 3).

The volume pulse sensor 50 is essentially block-shaped, for example roughly a cube. The back side of the volume pulse sensor 50 has a stop or holding or clamping screw 55 screwed therein, which passes through a pressure plate 56 formed with a groove 57 which, in turn, receives the horizontal portion 48 of the bail 42. The second stop or clamping nut 55, just as the first stop nut 26, has a circular knob 58, a cylindrical portion 59 coaxial with the knob and a threaded portion 60 projecting from the cylindrical part 59.

OPERATION

Figure 2:
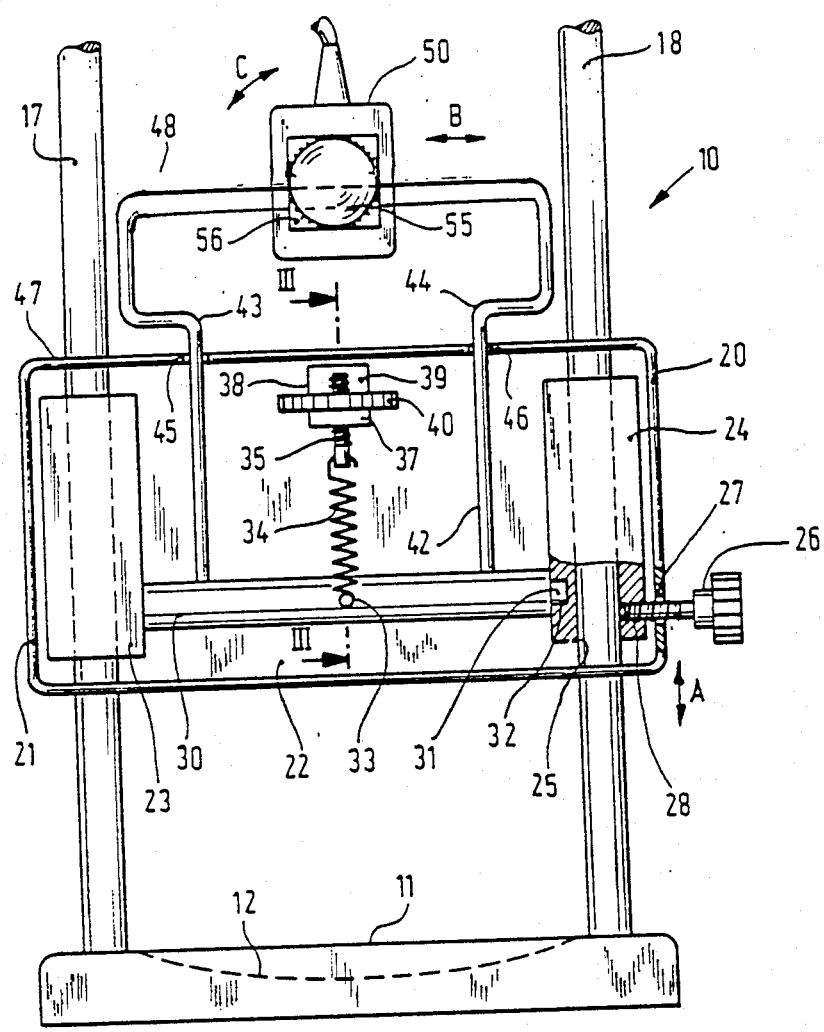
FIG. 2 is a back end view of FIG. 1, from right to left.

The patient, preferably lying stretched out on an examining table, places the heel 13 so that the apparatus 10 can be pushed thereunder. The heel 13 can rest in the depression 12 of the base plate 11. The clamping screw 26 is loosened, and the support element is so adjusted vertically—see arrow A of FIG. 2—that the center of the toe 61 of the foot 14 is aligned with the center of the forward side 53 of the volume pulse sensor 50. The forward side 53 forms the sensing surface thereof. The first clamping screw 26 is then tightened. The second clamping screw 55, see FIG. 1, is not tightened but only loosely turned, to shift the volume pulse sensor 50 horizontally, see arrow B of FIG. 2—to have optimal matching alignment with a toe 61 of the patient. This may be termed a y-axis adjustment. The sensor 50 can also be tilted about the horizontal axis, as shown by arrow C in FIG. 2, and turned horizontally about the transverse connecting element 48 of the bail 42, as shown by arrow D in FIG. 1. Optimal orientation with respect to an engagement surface with the toe 61 is thereby ensured. After rotating the sensor 50 in accordance with the arrows C and D, screw 55 is tightened. As the screw 55 is tightened, the cylindrical portion 59 thereof engages the pressure plate 56 which then presses the horizontal portion 48 of the bail 42 tightly against the back side of the volume pulse sensor 50. The horizontal portion 48 of the bail 42 is retained in groove 57 in the pressure plate 56. This, then, retains the volume pulse sensor 50 in the adjusted position without possibility of change or slippage. The force exerted by the spring 34 (FIG. 2) biases the volume pulse sensor towards the toe 61, which may be termed movement in the x-axis, upon rotation of the shaft 30. Spring 34 is adjusted by rotating the nut 40 (FIG. 3) which moves the threaded bolt 35 up or down. Measuring can be started as soon as the adjustment of the spring force is terminated. Although the movement is not exactly in the x-axis, but rather in a curve path about the pivots 31, the distance is so small that the vertical displacement due to the movement in an arc can be neglected.

Preferably, posts 17, 18 and the bail 42 as well as the shaft 30, are made of stainless steel; the housing 15 as well as housing 21 are preferably made of heat-insulating or poorly heat-conductive plastic material.

Various changes and modifications may be made within the scope of the inventive concept.

We claim:

1. Vasometric test apparatus for testing blood supply to a toe (61) of the foot (14) of a patient, comprising
   a base plate (11) formed with a depression to receive the heel (13) of the foot of the patient and thereby locate the foot of the patient with respect to a predetermined position on the base plate, whereby the foot is in upright vertical position;
   an upstanding support structure (17, 18) projecting from the base plate (11) and extending vertically at an essentially right angle to the base plate;
   a support element (20) adjustably positioned on the support structure (17, 18), said support element having a back wall (22) positioned for contacting the underside of the foot (14) of the patient in an essentially upright or vertical position, with the toe (61) projecting vertically;
   a pulse sensor (50) having a sensing surface (53), supported from said support element (20) for contact with the toe of the patient; and
   means for placing said pulse sensor to align the sensing surface (53) thereof with the toe of the patient and in controlled resilient position with respect to the toe of the patient when the heel (13) of the patient's foot is in said depression and extending vertically, and the foot is resting against said back wall (22) of the support element,
   said sensor placing means including means (26, 34, 40, 55, 60) for controllably resiliently supporting said pulse sensor (50) on said support element (20) for controlled resilient positioning with respect to the toe of the patient, and for controlled movement in three dimensions of the pulse sensor with respect to said base plate (11), whereby said pulse sensor can be aligned with the toe of the patient.

2. The apparatus of claim 1, wherein said upstanding support structure (17, 18) comprises two posts (17, 18) secured to the base plate;
   said support element (20) includes vertical slide means (23, 24) slidably (A) engaging said posts;
   and clamping means (26) are provided for clamping said vertical slide means on at least one of the posts, said slide means and clamping means forming part of said sensor placing means.

3. The apparatus of claim 2, wherein the support element (20) further comprises a bail (42) of general U-shape, tiltable about an axis transverse to said posts, and having an essentially horizontal portion (48);
   and wherein the pulse sensor (50) is slidable (B) on said essentially horizontal portion (48).

4. The apparatus of claim 3, wherein the controllable resilient support means includes a sensor clamping screw (55) threadably received in a back side (54) of the pulse sensor (50);
   a clamping plate (56) clamping a section of the horizontal portion (48) of the bail (42) against the back side (54) of the pulse sensor (50), the clamping plate being formed with a groove (57) for receiving the horizontal portion (48) of the bail (42) and, upon tightening of the sensor clamping screw, retaining the sensor in adjusted position, rotatable about said horizontal portion (48) of the bail, as well as rotatable about an axis perpendicular to its sensing surface.

5. The apparatus of claim 3, wherein said controllable resilient support means includes resilient means (34) for holding said U-shaped bail (42) resiliently movable about an essentially horizontal pivot axis.

6. The apparatus of claim 5, further including a shaft (30) extending transversely between the vertical slide means (23, 24) on the posts (17,18);

said shaft (30) rotatable about said pivot axis, said U-shaped bail (42) having longitudinal legs (43,44) coupled to said shaft (30), said shaft forming the horizontal pivot axis for the U-shaped bail.

7. The apparatus of claim 6, wherein the resilient means (34) comprises a spring (34) coupled to the shaft (30);

and means (40) for adjusting the spring force between said shaft and said bail.

8. The apparatus of claim 7, including a holding pin (33) extending from said shaft (30) at an essentially right angle with respect to the legs (43, 44) of said bail, said spring being a tension spring coupled to said holding pin (33) with one end thereof;

said back wall (22) connected to said slide means, and adjustably retaining the other end of said tension spring (34).

9. The apparatus of claim 1, wherein the pulse sensor (50) is a reflection light sensor.

10. The apparatus of claim 1, wherein the base plate (11) is an elongated flat cup or trough-shaped structure closed off at the bottom by a bottom plate (16).

11. The apparatus of claim 1, wherein the support element (20) comprises a trough or tub-shaped housing (21) closed off at the back by said back wall (22);

wherein the pulse sensing placing means include slider means (23, 24) for slidably supporting the support element (20) on said upstanding support structure (17, 18) and located within the trough or tub-shaped housing and the means for resiliently supporting the pulse sensor includes a pivot shaft (30) and a generally U-shaped bail (42) coupled to the shaft and projecting therefrom, said pulse sensor being mounted on said bail;

spring means (34) are provided for controlled resilient engagement of the pulse sensor with the toe of the patient, said spring means being coupled to the shaft, and to the housing, respectively, the spring means resiliently restraining pivoting of the shaft, said shaft, bail and the spring means being retained within said housing;

and wherein an adjustment means (40) is provided, coupled to the spring means (34) for adjusting the spring tension, said adjustment means projecting outside of said housing.

12. The apparatus of claim 1, wherein the resilient support means additionally includes means for permitting rotary movement of the pulse sensor (50) with respect to an axis perpendicular to its sensing surface (53).

13. The apparatus of claim 1, wherein said controllable resilient support and controllable movement means permit adjustment of the pulse sensor (50), with respect to the base plate in a horizontal direction transversely (B) to the foot of the patient; in a vertical direction longitudinally (A) to the foot of the patient; tilting movement (D) of the pulse sensor (50) with respect to a vertical direction perpendicular to the base plate (11) and extending longitudinally to the foot of the patient; and rotational movement (C) of the pulse sensor about an axis perpendicular to its sensing surface (53).

14. The apparatus of claim 1, wherein said support element comprises a trough or tub-shaped housing (21), said trough or tub-shaped housing including said back wall (22);

slider means (23, 24) are provided, slidable on said upstanding support structure (17, 18) secured to said trough or tub-shaped housing for vertically positioning said trough or tub-shaped housing to permit engagement of the foot (14) of the patient thereagainst;

and a generally U-shaped bail (42) tiltable about an axis parallel to a plane defined by said base plate (11) and having an essentially horizontal portion (48); and wherein the pulse sensor (50) is slidable (B) on said essentially horizontal portion (48) of the bail (42) and tiltable about an axis defined by said essentially horizontal portion.

15. The apparatus of claim 14, wherein said controllable resilient support means includes resilient means (34) for holding said U-shaped bail (42) resiliently movable about an essentially horizontal pivot axis.

16. The apparatus of claim 15, further including a shaft (30) extending transversely between the vertical slider means (23, 24) on the posts (17, 18);

said shaft (30) rotatable about said pivot axis, said U-shaped bail (42) having longitudinal legs (43, 44) secured to said shaft (30), said shaft forming the horizontal pivot axis for the U-shaped bail.

17. The apparatus of claim 16, wherein the resilient means (34) comprises a spring (34) coupled to the shaft (30);

and means (40) for adjusting the spring force between said shaft and said bail.

* * * * *